United States Patent [19]

McPherson

[11] Patent Number: 5,281,205
[45] Date of Patent: Jan. 25, 1994

[54] VASCULAR ACCESS SYSTEM AND CLEARING METHOD

[76] Inventor: William E. McPherson, 14605 Anchoret Rd., Tampa, Fla. 33625

[21] Appl. No.: 850,695

[22] Filed: Mar. 11, 1992

[51] Int. Cl.$^5$ .......................................... A61M 25/00
[52] U.S. Cl. .................................................... 604/267
[58] Field of Search ................. 604/175, 267, 50, 165, 604/51; 128/264, 280, 200, 201, 202, 203, 204, 205, 206, 244, 772

[56] References Cited

U.S. PATENT DOCUMENTS

| | | |
|---|---|---|
| 396,754 | 1/1889 | Mayfield . |
| 958,854 | 5/1910 | Bunn . |
| 3,416,532 | 12/1968 | Grossman . |
| 3,490,438 | 1/1970 | Lavender et al. . |
| 3,491,756 | 1/1970 | Bentov . |
| 3,595,241 | 7/1971 | Sheridan . |
| 4,274,408 | 6/1981 | Nimrod . |
| 4,525,157 | 6/1985 | Vaillancourt . |
| 4,585,440 | 4/1986 | Tchervenkov et al. . |
| 4,673,394 | 6/1987 | Fenton, Jr. et al. . |
| 4,710,167 | 12/1987 | Lazorthes . |
| 4,778,452 | 10/1988 | Moden et al. . |
| 4,790,812 | 12/1988 | Hawkins, Jr., et al. . |
| 4,854,325 | 8/1989 | Stevens . |
| 4,861,341 | 8/1989 | Woodburn . |
| 5,030,205 | 7/1991 | Holdaway et al. . |
| 5,030,213 | 7/1991 | Rumberger et al. . |
| 5,041,098 | 8/1991 | Loiterman et al. . |
| 5,109,850 | 5/1992 | Blanco et al. .......................... 604/50 |

FOREIGN PATENT DOCUMENTS 1297475  5/1962  France .

Primary Examiner—C. Fred Rosenbaum
Assistant Examiner—Manuel Mendez
Attorney, Agent, or Firm—William A. Birdwell & Associates

[57] ABSTRACT

A vascular access system and clearing method. A vascular access system is provided comprising an implantable access port for receiving medication transdermally, a catheter connected to an outlet in said port for infusing that medication into the blood stream, a wire for clearing the catheter of an obstruction, and a non-coring needle for inserting the wire transdermally into the access port and catheter. The access port includes a chamber for receiving medication, the chamber having an outlet whose bottom portion is substantially flush with the bottom portion of the chamber outlet to promote emptying of the chamber and feeding the guide wire into the outlet. The catheter is attached to the port by placing it over a cannula connected to the outlet and forcing a sleeve over the end of the catheter. An obstruction is cleared from the catheter by inserting the needle transdermally into the chamber, feeding the wire into the needle, tilting the needle so as to move the opening of the needle near the outlet of the chamber and feeding the wire from the opening of the needle through the outlet into the catheter to force all or a portion of the obstruction out of the way. The wire is then removed and an anti-fibrolitic material is injected transdermally to dissolve some or all of the remaining obstruction. Such an anti-fibrolitic material may also be used to soften the obstruction prior to forcing it out of the way with the wire.

13 Claims, 2 Drawing Sheets

VASCULAR ACCESS SYSTEM AND CLEARING METHOD

BACKGROUND OF THE INVENTION

This invention relates to vascular access systems implanted in individuals for the infusion of medication, and particularly to vascular access systems which can be cleared of obstructions in place and methods for clearing such systems.

In the treatment of many illnesses it is necessary to infuse medication directly into the bloodstream periodically. To avoid having to locate a blood vessel for injection by a needle each time, it is desirable to implant a catheter into the circulatory system through which the medication is infused. To avoid having a catheter extend through the skin, which presents a danger of infection as well as considerable inconvenience and discomfort, the catheter is terminated at a vascular access port implanted beneath the skin and having a self sealing membrane penetrable by a needle for injecting the medication. Often, the medication is toxic in concentrated amounts and, therefore, must be infused through a catheter into a large volume of blood. To accomplish this, the catheter is fed through a vessel to a chamber of the heart. This combination of components is typically referred to as a vascular access system.

A problem that arises with implanted vascular access systems is that, despite steps taken after they are used to keep them clear, the catheter often becomes clogged with coagulated blood or other material between usages and is difficult to clear for use again. When there is an obstruction in an implanted infusion port there are basically two known approaches for solving the problem. One is to inject a dissolving agent such as heparin to try to dissolve the obstruction. Often this does not work, so the second approach must be used, which is to remove and replace the system. However, replacing the access system is dangerous, not only because it is an invasive procedure, but because removal of the system usually causes debris on the catheter to break away and enter the blood stream, which presents a risk of blockage of blood circulation to parts of the body.

One device previously known for clearing salt blockages in a drainage catheter is disclosed in Rumberger et al. U.S. Pat. No. 5,030,213, issued Jul. 9, 1991. However, this device is only suitable for a catheter whose proximal end extends outside of the body so that a router wire can be inserted into the catheter and a pin vice can be attached to the end of the catheter for rotating the router wire. Such a pin vice and router wire cannot be used with an implanted vascular access system.

Hawkins, Jr. et al. U.S. Pat. No. 4,790,812, issued Dec. 13, 1988, and Stevens U.S. Pat. No. 4,854,325, issued Aug. 8, 1989, both disclose devices and methods for removing an obstruction in a blood vessel. In Hawkins, Jr. et al. a cable with a cutting tip on its end is housed within a catheter which is inserted into the blood vessel. The cutting tip is pushed out the end of the catheter and rotated by the cable to fragment an obstruction. In Stevens, a guide wire is housed within a catheter inserted in the blood vessel so that the tip of the wire extends slightly beyond the tip of the catheter. The guide wire is caused to reciprocate at high speed to ram the tip through an obstruction. However, both of these devices and methods also employ a catheter whose proximal end extends outside the body and which would not be suitable for an implanted vascular access system.

Accordingly, there is a need for a vascular access system and clearing method for periodic infusion of medication wherein communication of the system with the exterior of the body is minimized and the catheter portion of the system may be cleared without removal of the system from the patient.

SUMMARY OF THE INVENTION

The present invention meets the aforementioned need by providing a vascular access system having a novel combination of components which facilitates a novel method for clearing a catheter in the system while an implantable portion of the system remains entirely within the body. The system employs an implantable access port with a chamber, having a bottom portion, a substantially perpendicular side wall forming an opening opposite the base, a self-sealing membrane or septum covering the opening, and an outlet in the side wall. A catheter is connected to the outlet by a cannula and sleeve assembly for the passage of fluid therethrough. A bottom portion of the interior surface of the outlet forms a smooth transition with the bottom portion of the chamber, and is preferably flush with the bottom portion of the chamber, to permit a guide wire to be fed from the interior of the chamber into the outlet. A Huber-type needle is provided for inserting the guide wire through the septum into the chamber. The needle has a tip and an opening adjacent the tip askew to the longitudinal axis of the needle so that when the needle is inserted through the septum, it does not cut a plug out of the septum.

The method for clearing the system comprises inserting the needle through the septum into the chamber, feeding a guide wire through the needle into the chamber, orienting the opening of the needle toward the outlet of the chamber, feeding the wire through the chamber into the outlet and feeding the wire through the catheter to the obstruction in the catheter to force all or a portion of the obstruction out of the way, thereby allowing fluid to pass therethrough. Preferably, after the needle is inserted through the septum and its opening is oriented toward the outlet, it is tilted so as to place the opening near the outlet and thereby enhance the ease with which the guide wire may be fed from the needle into the outlet. Also, during the feeding of the wire from the needle into the outlet, it is often helpful to maintain the tip of the needle slightly above the bottom portion of the chamber. Thereafter, the guide wire is removed and an anti-fibrolitic fluid is injected into the chamber through the septum so as to dissolve all or a portion of the remaining obstruction, thereby enhancing the likelihood that the catheter will remain clear. An anti-fibrolitic fluid may also be injected prior to insertion of the Huber-type needle and guide wire to soften the obstruction.

The foregoing and other objectives, features and advantages of the invention will be more readily understood upon consideration of the following detailed description of the invention, taken in conjunction with the accompanying drawings.

DESCRIPTION OF THE PREFERRED EMBODIMENT

Figure 1:
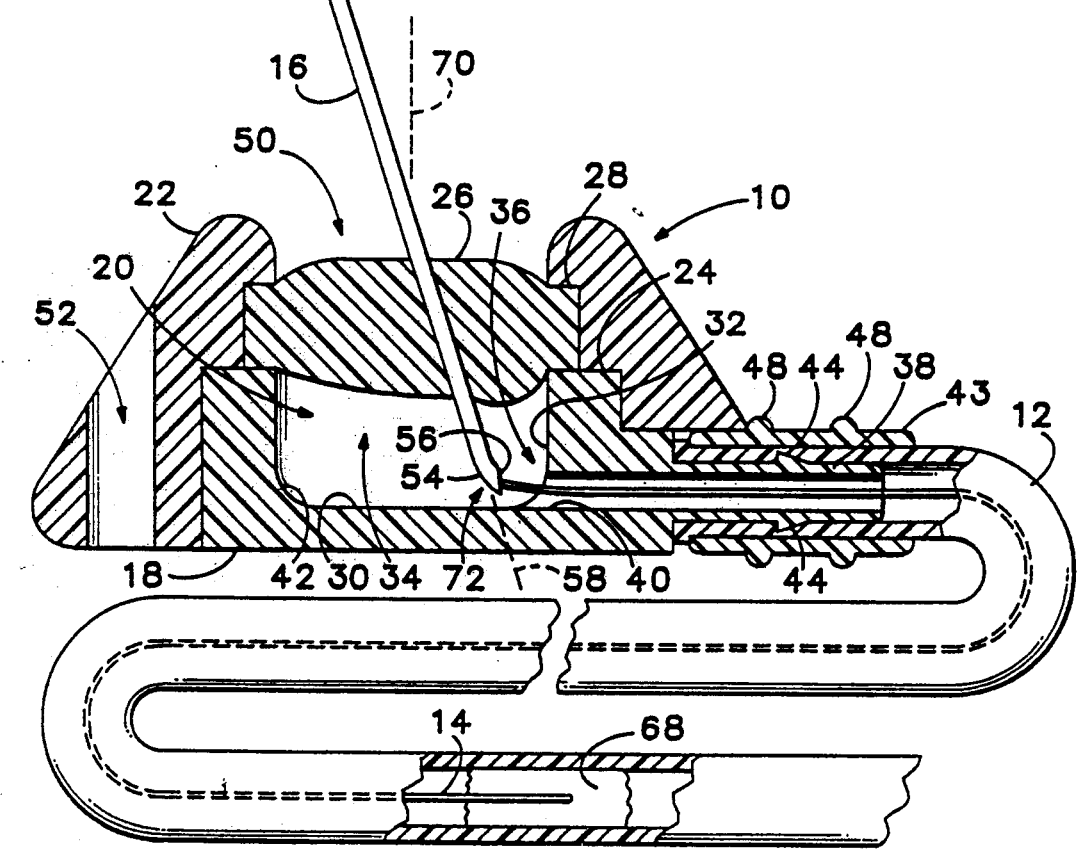
FIG. 1 shows a side cross section of a vascular access system and method of use in accordance with the present invention.

A preferred embodiment of a vascular access system and the method for clearing the system is shown in FIG. 1. The system comprises an access port 10, a catheter 12, connected to the access port, a wire 14 for removing an obstruction in the catheter and a needle 16 for inserting the wire 14 into the access port. The access port 10 comprises a core 18, having a chamber 20 therein, and a base 22. Preferably, the core 18 is generally cylindrical in shape and the base 22 is generally annular in shape, the core fitting inside the base from the bottom thereof and abutting against a first lip 24 of the base. The chamber 20 is covered by a septum 26 made of a self-sealing, penetrable elastomer which is disposed between the core 18 and a second lip 28 of the base 22. The core and base are preferably made of a plastic material, such as that material marketed under the trademark DELRIN by E. I. du Pont De Nemouns and Company of Wilmington, Delaware, and the dimensions of the core, septum and base should be made so that they will snap fit snugly together. It is to be recognized, however, that other materials may be used without departing from the principles of the invention.

The chamber 20 is formed of a bottom portion 30, opposite the septum 26, and an interior side wall 32, thereby providing an opening 34 covered by the septum. Preferably, the opening 34 is substantially circular in shape, so that there is only one side wall, though it is to be recognized that other shapes might be employed without departing from the principles of the invention. An outlet 36 for the chamber is disposed in the side wall 32 and connects with a cannula 38 attached to the side wall for receiving the catheter 12. The outlet 36 and cannula 38 form a fluid flow channel into the catheter. Preferably, a bottom portion 40 of the interior surface of the outlet is disposed flush with the bottom portion 30 of the chamber, not only to facilitate emptying of the chamber into the catheter 12, but also to facilitate insertion of the guide wire 14 into the outlet, as will be explained hereafter. In addition, the junction 42 between the side wall 32 and the bottom portion 30 of the chamber preferably forms a smooth, concave curve with respect to the interior of the chamber. This also facilitates guiding of the wire 14 into the outlet 36, and minimizes the opportunity for formation of deposits.

Figure 2:
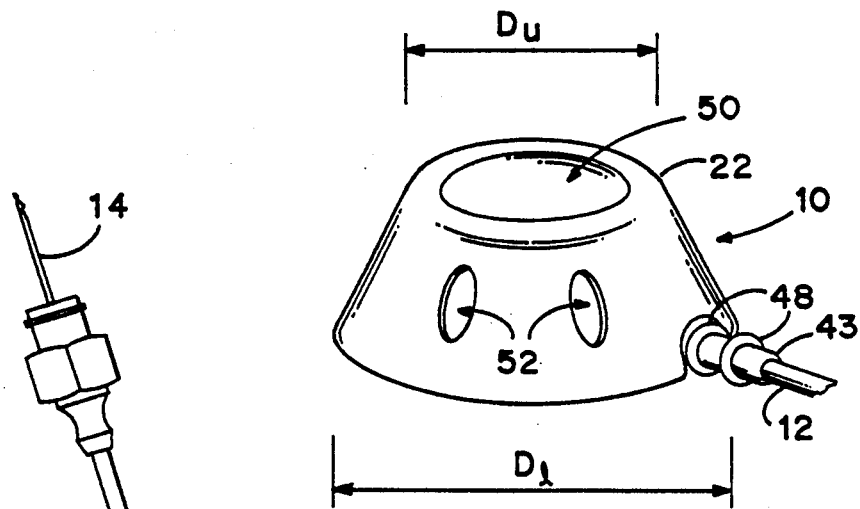
FIG. 2 shows a perspective view of a vascular access port and a portion of a catheter attached thereto in accordance with the present invention.

The catheter 12 fits over the cannula 38 and is held in place by a sleeve 43 placed over the catheter and forcibly snapped into place over the end of the catheter and the cannula, as shown in FIG. 2 as well as FIG. 1. The cannula 38 has radially protruding barbs 44 for restraining the catheter when the sleeve 43 is in place. The sleeve also includes a pair of rings 48 around the exterior thereof for gripping the sleeve to snap it in place over the cannula. The catheter is preferably made of a flexible, plastic material such as the tubing marketed under the trademark TECOFLEX by Thermedics Incorporated of Woburn, Mass. Ideally, it should have an internal diameter of about 0.062 inches and an outside diameter of about 0.112 inches and should withstand pressure as high as 70 psi. However, it is to be recognized that other materials and dimensions might be used without departing from the principles of the invention.

The access port 10 is generally frustrum shaped, as shown in FIG. 2, with a base lower outside diameter D1 of about 1.250 inches and a base upper outside diameter Du of about 0.750 inches. An upper opening 50 to the septum 26 is provided and should be about 0.500 inches in diameter. Suture holes 52 are disposed around the periphery of the base 22 for enabling the access port to be stitched to patient tissue so as to be held in place.

The needle 16, which may be attached to any suitable handle (not shown), is a non-coring needle of the Huber type. That is, its tip 54 has an opening 56 which is askew to the longitudinal axis 58 of the needle. This ensures that, when the needle is inserted through the septum 26, it does not cut a plug in the septum.

The outside diameter of the wire 14, which is preferably about 0.021 inches, establishes the minimum inside diameter of the needle 16. The wire 14 must have sufficient flexibility to be fed through the needle 16, into the outlet 36 of the access port 10 and down the catheter 12. A stainless steel catheter guide wire of the type generally known in the art has been found to be acceptable. This size of wire is preferred because it is the largest diameter wire that will fit within a 19 gauge Huber-type needle, which is generally the largest gauge needle that allow at least about 1000 sticks into the septum.

Figure 3:
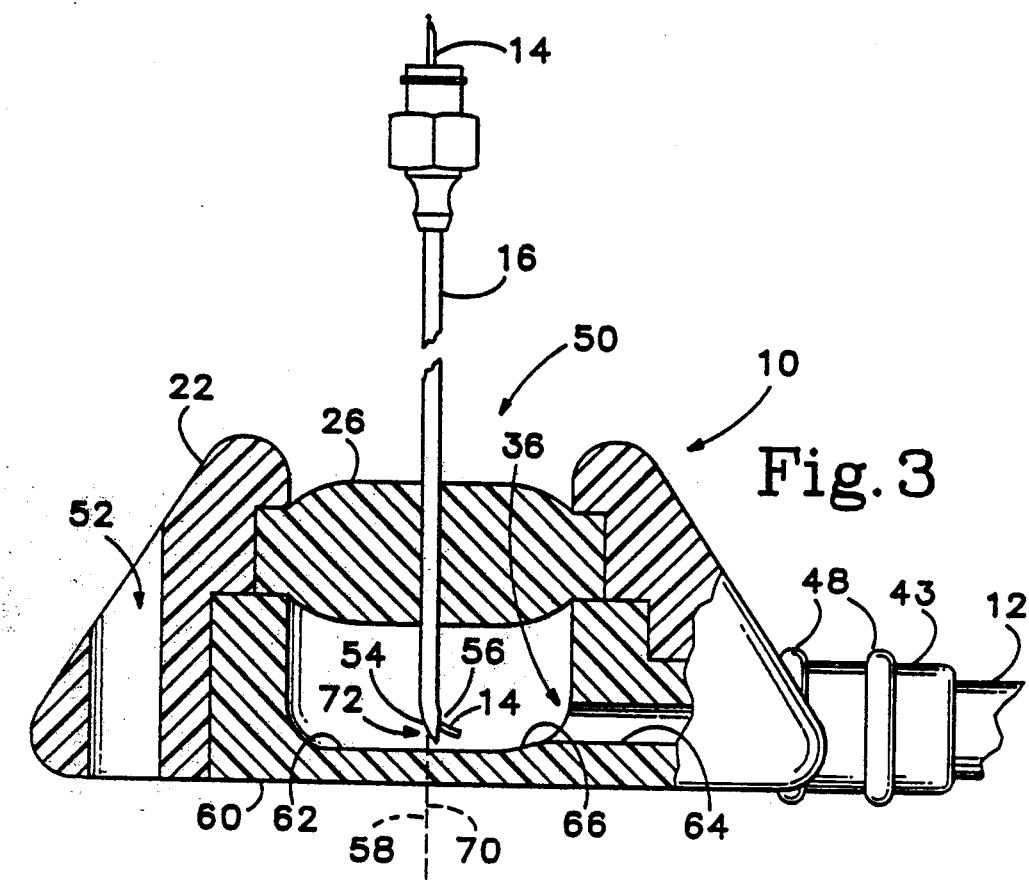
FIG. 3 shows a side, partial cross section of an alternative vascular access port according to the present invention.

An alternative embodiment of the access port 10 is shown in FIG. 3. In this embodiment, a core 60 has a bottom portion 62 which is slightly lower than the bottom portion 64 of the interior surface of the outlet 36. A smooth transition 66 is formed between the bottom portion 62 and the bottom portion 64 in this embodiment to facilitate guiding the wire 14 into the outlet 36, as shown in FIG. 4 and explained hereafter.

The implantable portion of the system is assembled by snapping the base 22, septum 26 and core 18 together; then placing the sleeve 42 over the catheter 12, placing the end of the catheter 12 over the cannula 38, and forcing the sleeve into place. This portion of the system is then surgically implanted in a person. The catheter is typically fed into the vasculature, down a vessel to the heart. The access port 10 is placed just beneath the epidermis and above the musculature of the person. Thereafter, the chamber 20 of the access port 10 is accessed transdermally with a needle for extracoporeal treatment of the patient and for clearing of the system, as will be explained hereafter.

The method of the invention is explained with particular reference to FIGS. 1 and 3. In FIG. 1, an obstruction 68, such as a blood clot, is shown disposed in the catheter 12. The object of the method is to displace and dissolve all or a portion of that obstruction so as to clear the passage way of the catheter 12 for fluid flow. This is accomplished by first inserting the needle 16 through the septum 26 with the elongate axis 58 of the needle substantially parallel to the central vertical access 70 of the access port 10. This minimizes the amount of septum material that the needle must pass though. Thereafter, the wire 14 is fed into the needle and slightly out the opening 56 in the tip 54 of the needle. The opening is oriented toward the outlet 36 of the chamber. Then, the needle is tilted to move the tip 54 closer to the outlet 56, as shown in FIG. 1, thereby making it easier to feed the wire 14 into the outlet 36. This causes the septum to become distorted in shape, as shown in FIGS. 1 and 4, but it will later restore itself to its original shape when the needle is released or removed. During this process the tip is preferably maintained slightly above the bottom surface of the core, as indicated by gap 72. This also facilitates guiding the wire into the outlet 36. The wire is then fed down the catheter 12 to the obstruction 68 and pushed forward to either poke through the obstruction or push the obstruction out the end of the catheter. The wire is then removed, and an anti-fibrolitic fluid, such as Heparin, is injected into the chamber by a syringe (not shown) to dissolve all or a portion of the remaining obstruction. In addition, or as an alternative, such an anti-fibrolitic fluid may be injected into the chamber prior to insertion of the needle 16 so as to soften the obstruction prior to use of the wire 14.

Figure 4:
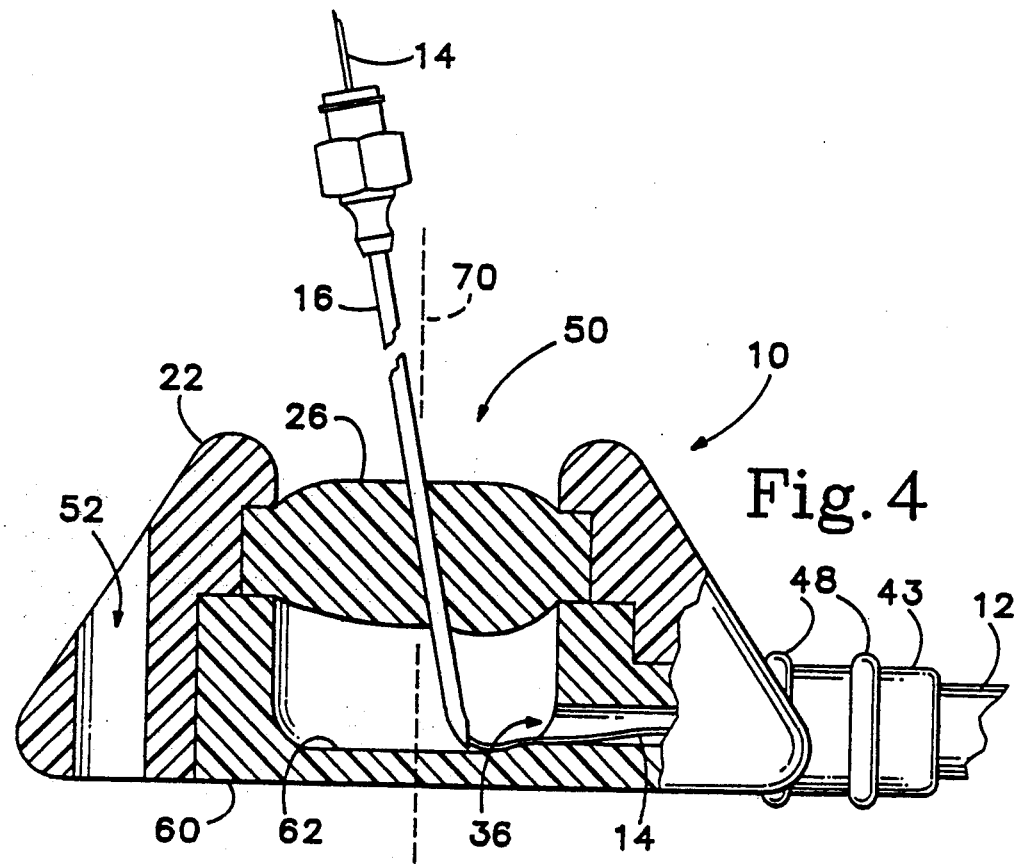
FIG. 4 shows a side, partial cross section of a vascular access system employing the port of FIG. 3 where a wire has been fed into a catheter of the system.

As shown in FIG. 4, in the alternative embodiment of the access port, the wire 14 slides over the smooth transition 66. That transition prevents the wire from getting caught on the interior of a chamber.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A method for clearing an obstruction from a vascular access system having an access port, with a chamber for receiving medication, a septum covering the chamber and an outlet from the chamber, and a catheter connected to the outlet of the chamber, said method comprising:
   (a) inserting a non-coring needle transdermally through said septum chamber, said needle having an opening at its tip askew to the longitudinal axis thereof;
   (b) feeding a wire into said needle;
   (c) orienting said opening toward said outlet of said chamber;
   (d) feeding said wire out of said opening of said needle into said outlet; and
   (e) feeding said wire through said catheter to force a portion of said obstruction out of the way.

2. The method of claim 1, wherein said chamber has a bottom portion opposite said septum, said method further comprising positioning said tip of said needle slightly above said bottom portion while feeding said wire out of said opening into said outlet.

3. The method of claim 1, further comprising tilting said needle relative to said access port so that said tip moves toward said outlet.

4. The method of claim 1, further comprising, after step (e), removing said wire and said needle and injecting into said access port an anti-fibrolitic material to dissolve a portion of said obstruction.

5. The method of claim 1, further comprising, prior to or during step (e), injecting into said access port an anti-fibrolitic material to soften said obstruction.

6. The method of claim 1, wherein said chamber has a bottom portion opposite said septum and a side wall between said septum and said bottom portion, said side wall forming a joint with said bottom portion that is substantially smooth and concave with respect to the interior of said chamber.

7. The method of claim 1, wherein said chamber has a bottom portion opposite said septum and a side wall between said septum and said bottom portion of said chamber, the interior surface of said outlet having a bottom portion substantially flush with said bottom portion of said chamber.

8. The method of claim 1, wherein said chamber has a bottom portion opposite said septum and a side wall between said septum and said bottom portion of said chamber, said bottom portion of said chamber being lower than said bottom portion of said outlet and said side wall forming a substantially smooth transition between said bottom portion of said chamber and the interior surface of said outlet.

9. A vascular access system, comprising:
   (a) an access port having a chamber with a bottom portion, a side wall extending away from said bottom portion to form a chamber opening, a septum covering said opening and an outlet in said side wall, said outlet having an interior surface forming a smooth transition with said bottom portion of said chamber;
   (b) a catheter connected to said outlet so as to pass fluid therebetween;
   (c) a wire having a predetermined diameter; and
   (d) non-coring needle means for transdermal insertion into said chamber through said septum, said needle means having a tip and an opening disposed at said tip, said opening being askew to the longitudinal axis of said needle means, and for feeding said wire through said needle means, out said opening therein, through said outlet and through said catheter to clear an obstruction therein.

10. The system of claim 9, wherein said bottom portion of said outlet is substantially flush with said bottom portion of said chamber.

11. The system of claim 9, wherein said bottom portion of said chamber is lower than said bottom portion of said outlet.

12. The system of claim 9, further comprising a cannula disposed on said access port at said outlet to said chamber for attachment of said catheter by placement of said catheter over said cannula.

13. The system of claim 12, further comprising a sleeve disposed over said catheter for securing said catheter on said cannula.

* * * * *